(12) United States Patent
Rossi

(10) Patent No.: US 6,579,264 B1
(45) Date of Patent: Jun. 17, 2003

(54) DEVICE FOR PUTTING A CATHETER TUBE INTO PLACE IN A VEIN

(75) Inventor: Daniel Rossi, Meriel (FR)

(73) Assignee: Vygon, Ecouen (FR)

( * ) Notice: Subject to any disclaimer, the term of this patent is extended or adjusted under 35 U.S.C. 154(b) by 0 days.

(21) Appl. No.: 09/581,374

(22) PCT Filed: Oct. 12, 1999

(86) PCT No.: PCT/FR99/02451

§ 371 (c)(1), (2), (4) Date: Aug. 9, 2000

(87) PCT Pub. No.: WO00/21603

PCT Pub. Date: Apr. 20, 2000

(30) Foreign Application Priority Data

Oct. 13, 1998 (FR) .............................. 98 12785

(51) Int. Cl.⁷ .............................. A61M 25/06
(52) U.S. Cl. ............................ 604/166.01; 604/164.05; 604/164.1
(58) Field of Search ................ 604/158–163, 604/164.05, 164.07, 164.1, 164.01, 506–508

(56) References Cited

U.S. PATENT DOCUMENTS

| | | | | |
|---|---|---|---|---|
| 3,082,769 A | * | 3/1963 | Palmer | 604/166.01 |
| 3,388,703 A | | 6/1968 | Bowes | |
| 3,612,050 A | * | 10/1971 | Sheridan | 604/166.01 |
| 4,995,866 A | * | 2/1991 | Amplatz et al. | 604/166.01 |
| 5,015,239 A | | 5/1991 | Browne | 604/166.01 |
| 5,431,676 A | * | 7/1995 | Dubrul et al. | 604/164.1 |
| 5,499,975 A | | 3/1996 | Cope et al. | 604/164.1 |
| 5,997,562 A | * | 12/1999 | Zadno-Azizi et al. | 604/158 |

FOREIGN PATENT DOCUMENTS

| | | |
|---|---|---|
| EP | 0 738 520 | 10/1996 |
| EP | 0 792 660 | 9/1997 |

* cited by examiner

Primary Examiner—J. Casimer Jacyna
(74) Attorney, Agent, or Firm—Levine & Mandelbaum

(57) ABSTRACT

A device for installing a catheter tube in a vein by the Seldinger method, once the device has been inserted, has a tubular cylindrical sheath, with a slot running its entire length, mounted on a dilator tube. A cylindrical main portion of the sheath terminates at a distal end edge which flares forwardly and is adjacent a shoulder of the dilator tube for enabling the dilator tube to be withdrawn through the sheath.

4 Claims, 5 Drawing Sheets

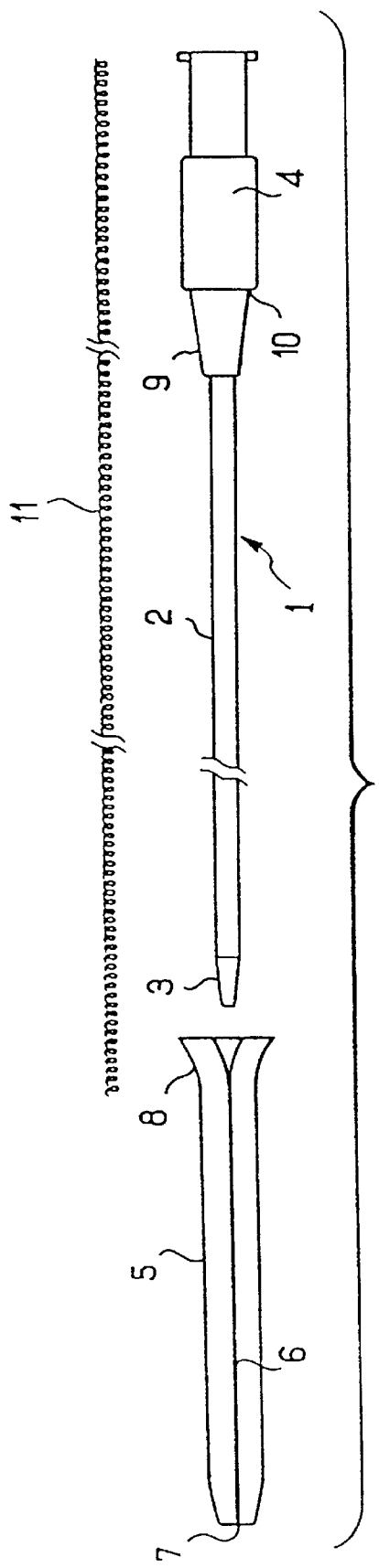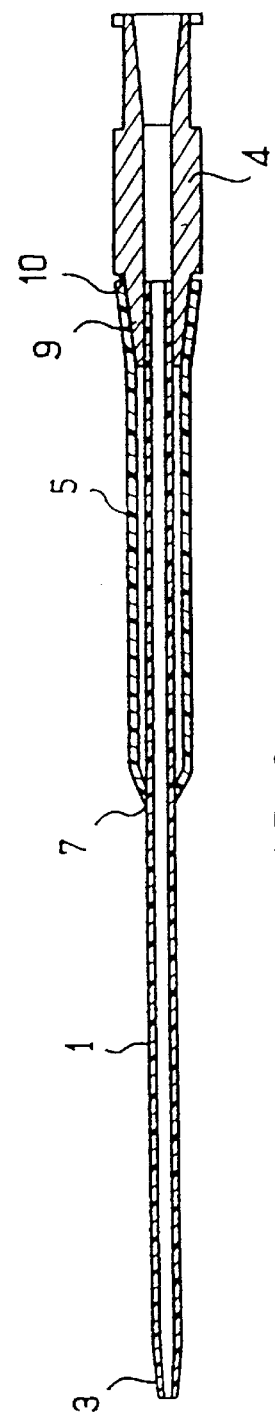

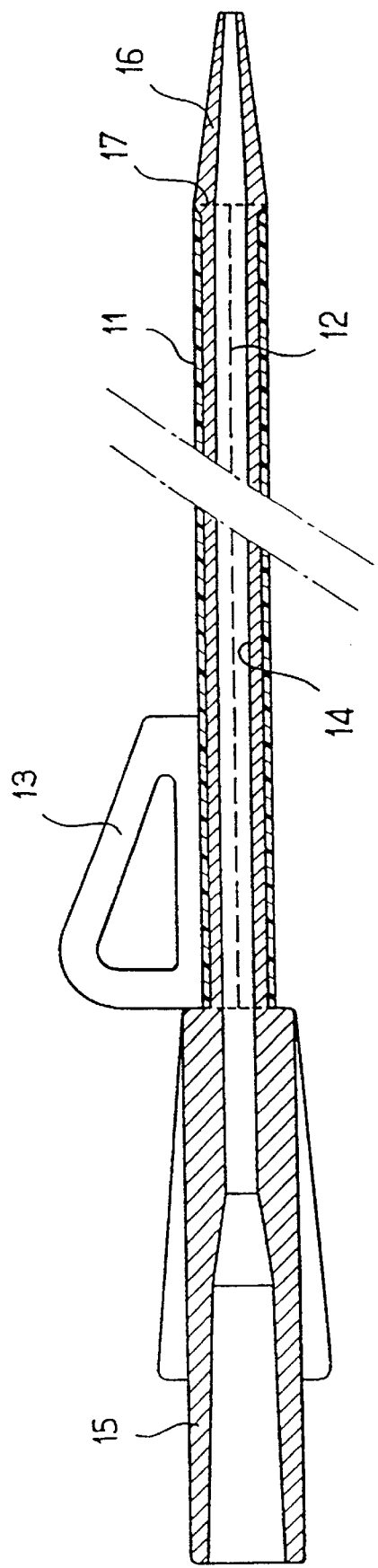

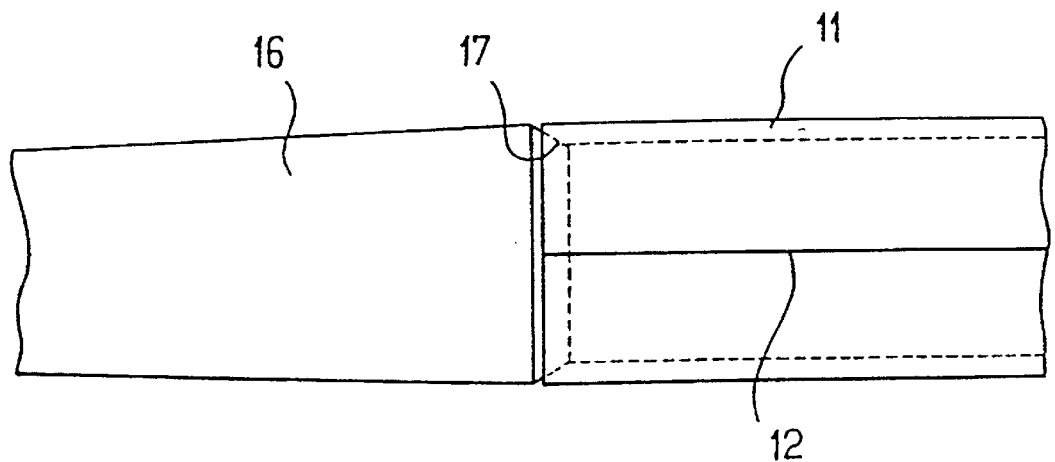
FIG_5
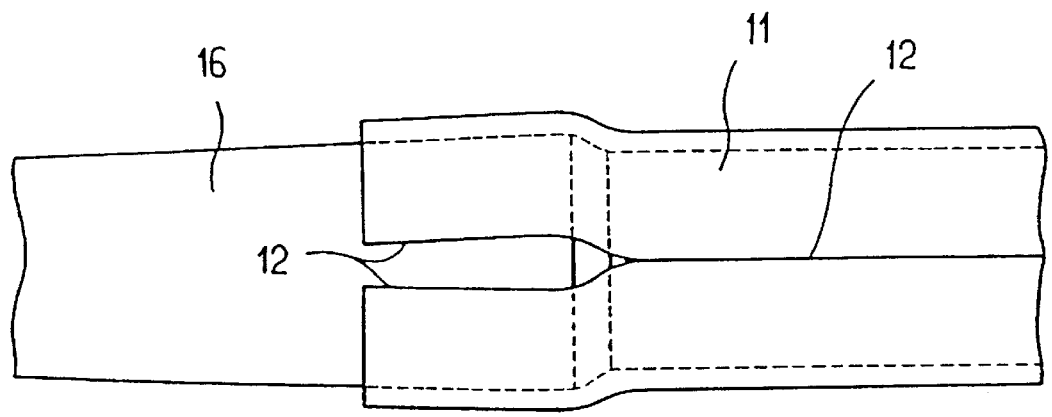
FIG_7

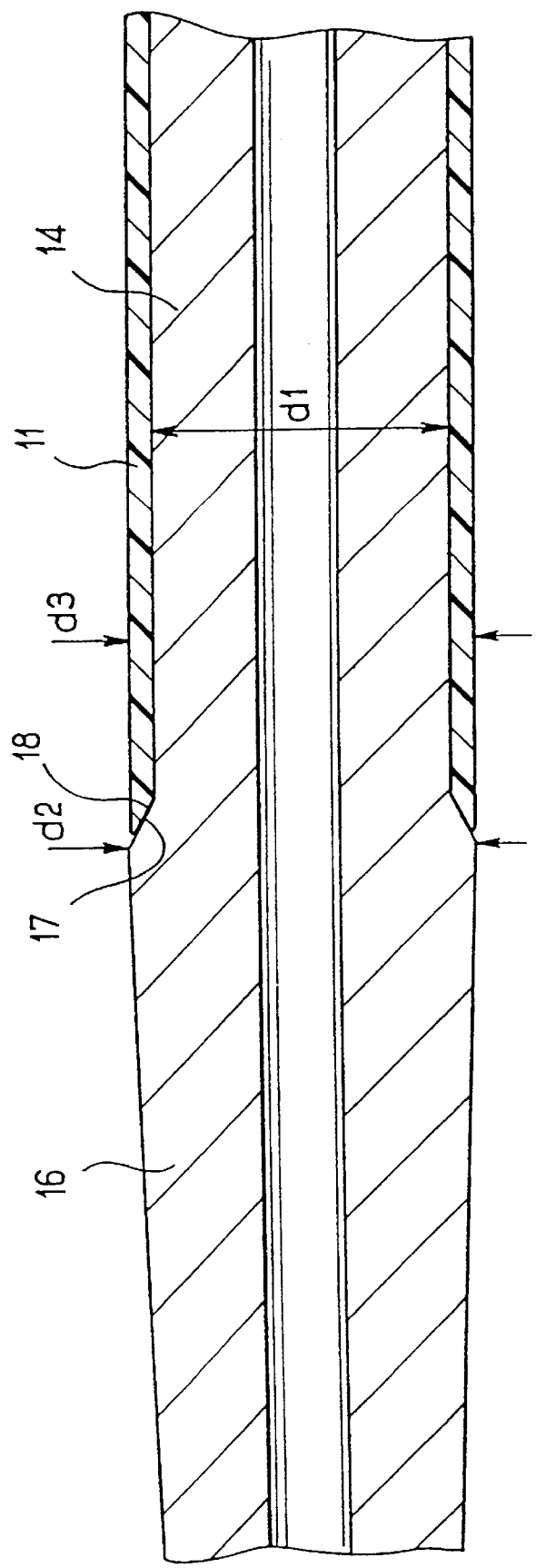
FIG_6

DEVICE FOR PUTTING A CATHETER TUBE INTO PLACE IN A VEIN

BACKGROUND OF THE INVENTION

1. Field of the Invention

The invention relates to a device having a tubular sheath associated with a "dilator" tube for putting a catheter tube into place in a vein after the device has been inserted by the "Seldinger" method.

2. Background of the Invention

This sildinger method requires the following operations:
1) puncturing the vein with a needle;
2) inserting a metal guide into the vein through the puncturing needle;
3) withdrawing the needle;
4) inserting an assembly constituted by a sheath threaded on a dilator tube over the metal guide;
5) withdrawing the dilator and the guide, leaving the sheath in place;
6) inserting the catheter in the sheath; and
7) withdrawing the sheath.

A problem arises in facilitating insertion of the sheath in the body and extracting it therefrom while reducing the risk of trauma.

Various solutions to that problem are described in the following publications: U.S. Pat. No. 5,499,975, U.S. Pat. No. 5,098,393, WO 99/21605, and EP 0 792 660.

Furthermore, publication FR-A-2 439 591 describes such a tubular sheath (5) which has a resilient slot (6) along its entire length, the distal end (7) thereof being blunted and which is threaded onto a dilator tube (1) whose distal end (3) is tapering.

The term "resilient slot" means that the lips of the slot can move apart from each other, but return towards each other when the cause of their moving apart has ceased.

To make it easier to pass through the skin and through the vein wall, the distal ends of the dilator and of the sheath are subjected to treatment:
the dilator tapers so as to obtain a slope whose distal end is as close as possible to the diameter of the guide; and
the sheath is made blunt so as to match the outside diameter of the dilator.

FIG. 1 of the accompanying drawings reproduces FIG. 1 of that publication, the sheath and the dilator being shown separately, while FIG. 2 of the drawings reproduces FIG. 2 of that publication, the sheath being shown threaded on the dilator.

Making the sheath blunt is a difficult operation.

It is necessary to conserve a distal flat (step) to prevent the sheath turning inside-out on passing through tissue.

The sensation of an abutment thus remains as it passes through tissue and the vein, and this gives rise to trauma.

SUMMARY OF THE INVENTION

The present invention seeks to remedy those drawbacks.

According to the invention, this is achieved with a device which comprises a sheath having a cylindrical main portion and which is split over its entire length by a resilient slot, said sheath being threaded onto a dilator tube which has a cylindrical main portion and a tapering distal end, and which presents the following features:
the distal end of the tube connects with the main portion of the tube via a shoulder that projects relative to said main portion;
the cylindrical main portion of the sheath terminates at a distal end edge which flares forwardly; and
the shoulder of the tube fits closely to the distal end edge of the sheath.

By means of this combination of characteristics, the tissues are passed through without coming into abutment and thus without trauma.

When the dilator is withdrawn, the slot of the sheath opens to allow the shoulder of the dilator to pass and then returns to its initial (closed) shape after the dilator has been fully withdrawn.

BRIEF DESCRIPTION OF THE DRAWINGS

An embodiment of the invention is described below with reference to the figures of the accompanying drawings, in which:

FIGS. 1 and 2, described above, reproduce FIGS. 1 and 2 respectively of the above-cited publication;

FIG. 3 is an axial section of an embodiment of a device having a sheath and a dilator of the present invention;

FIGS. 5 and 6 are views on a larger scale respectively of the elevation and the section of FIG. 4; and FIG. 7 is an elevation view corresponding to that of FIG. 5, but during withdrawal of the dilator.

DETAILED DESCRIPTION OF THE PREFERRED EMBODIMENT

Figure 4:
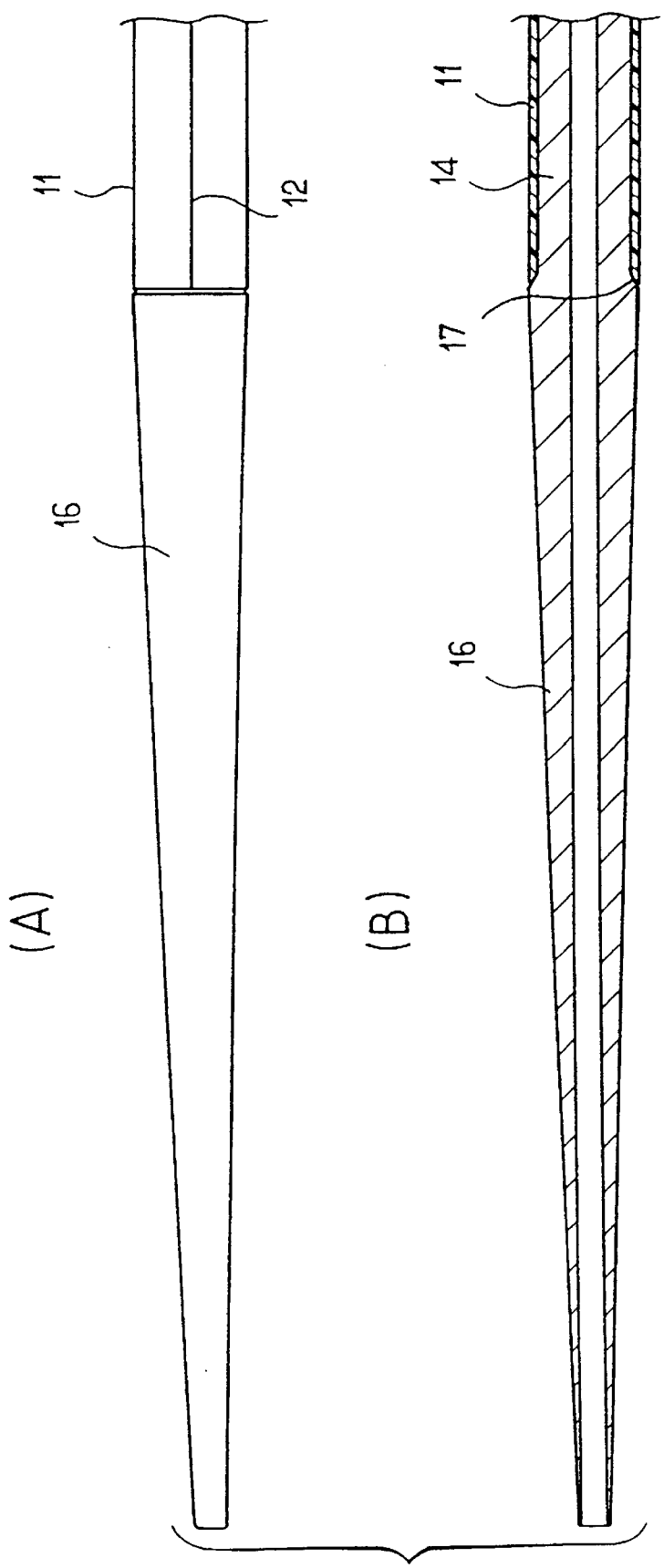
FIG. 4 is an elevation view (FIG. 4A) and a section view (FIG. 4B) of the distal ends of the sheath and the dilator of the device of the invention.

The device shown in FIGS. 3 to 6 comprises:
a cylindrical tubular sheath (11) that is longitudinally split at (12) over its entire length and that is provided at its proximal end (i.e. the end that remains closer to the manipulator) with a handle (13) for making it easier to grasp. The sheath is made in conventional manner out of a material enabling the slot to open under the effect of an element of outside diameter larger than the inside diameter of the sheath passing along the inside of the sheath, and to close up again on its own after said element has been withdrawn, thus providing that which is referred to above as a "resilient slot"; for example, the sheath can be a polyurethane tube whose inside and outside diameters lie in the range 1.5 mm to 5.5 mm; and
a cylindrical dilator tube (14) provided with a proximal coupling socket (15) and having a distal end (16) that tapers. This tube is made of synthetic resin, e.g. polypropylene.

In accordance with the invention, the distal end (16) of the dilator tube is connected to the main cylindrical portion (14) of the tube via a shoulder (17) that projects relative to said main portion.

The shape of this shoulder can be arbitrary but it is preferably given a frustoconical shape whose right section decreases from the front towards the rear, as in the example shown.

The end edge (18) of the distal end of the sheath (11) is frustoconical in shape, flaring towards the front in a manner that corresponds to the shape of the shoulder so as to fit closely thereto.

The outside diameter of the main proton of the tube (14) is selected to be substantially equal to the inside diameter (d1) of the sheath (11) so that the sheath is engaged on the tube with a certain amount of friction while the diameter (d2) of the tube at the greatest diameter of the shoulder is selected to be equal to or slightly greater than the outside diameter (d3) of the sheath so that the sheath does not project outwards at the shoulder.

What is claimed and desired to be secured by letters patent of the united states is:

1. A device comprising a tubular sheath and a dilator tube for installing a catheter tube in a vein by the Seldinger method once the device has been inserted, said sheath presenting a cylindrical main portion (11) and presenting over its entire length a resilient slot (12), said sheath being mounted on a tube which presents a cylindrical main portion (14) and whose distal end (16) tapers, the device having the following features:

the distal end of the tube connects with the main portion of the tube via a shoulder (17) that projects relative to said main portion;

the cylindrical main portion (14) of the sheath terminates at a distal end edge (18) which flares forwardly; and the shoulder (17) of the tube fits closely to the distal end edge (18) of the sheath.

2. A device according to claim 1, in which the distal end edge (18) of the sheath is frustoconical in shape.

3. A device according to claim 1, in which the outside diameter of the cylindrical main portion (14) of the tube is substantially equal to the inside diameter (d1) of the sheath so that the sheath is engaged on the tube with a certain amount of friction, while the diameter (d2) of the tube at the maximum diameter portion of the shoulder is equal to or slightly greater than the outside diameter (d3) of the sheath so that the sheath does not project outwards from the shoulder.

4. A device according to claim 1, in which the sheath is provided at its proximal end with a handle (13).

* * * * *